(12) United States Patent
Grafton

(10) Patent No.: US 7,820,638 B2
(45) Date of Patent: Oct. 26, 2010

(54) METHOD OF APPLYING HYALURONIC ACID TO IMPLANT OR GRAFT TO ENHANCE LUBRICITY AND CELLULAR DENSITY

(75) Inventor: R. Donald Grafton, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1459 days.

(21) Appl. No.: 10/635,444

(22) Filed: Aug. 7, 2003

(65) Prior Publication Data

US 2004/0180822 A1 Sep. 16, 2004

Related U.S. Application Data

(60) Provisional application No. 60/402,068, filed on Aug. 9, 2002.

(51) Int. Cl.
*A61K 31/726* (2006.01)
*A61K 31/728* (2006.01)
*C07H 5/06* (2006.01)
*C12P 19/04* (2006.01)

(52) U.S. Cl. .......................... 514/54; 514/56; 536/55.1; 536/123; 536/123.1

(58) Field of Classification Search .................... 514/54
See application file for complete search history.

(56) References Cited

U.S. PATENT DOCUMENTS

| | | | | | |
|---|---|---|---|---|---|
| 5,049,073 | A | * | 9/1991 | Lauks | ......................... 433/173 |
| 5,326,001 | A | * | 7/1994 | Holmquist et al. | ........... 222/387 |
| 5,515,590 | A | * | 5/1996 | Pienkowski | ................... 29/404 |
| 6,162,487 | A | * | 12/2000 | Darouiche | ................. 427/2.14 |
| 6,179,817 | B1 | * | 1/2001 | Zhong | ......................... 604/265 |
| 6,765,069 | B2 | * | 7/2004 | Zamora et al. | .............. 525/404 |
| 6,949,251 | B2 | * | 9/2005 | Dalal et al. | ................. 424/423 |
| 6,953,463 | B2 | * | 10/2005 | West, Jr. | ...................... 606/73 |
| 2003/0033021 | A1 | * | 2/2003 | Plouhar et al. | ........... 623/23.57 |

FOREIGN PATENT DOCUMENTS

WO WO 98/23094 11/1993

OTHER PUBLICATIONS

Habal et al. "Bone Grafts and Bone Substitutes" (1992) Published by W. B. Saunders Company, Chapter 32, pp. 378-407.*
D. R. Hunt et al., "Hyaluronan Supports Recombinant Human Bone Morphogenetic Protein-2 Induced Bone Reconstruction of Advanced Alveolar Ridge Defects in Dogs. A Pilot Study", J. Periodontol, vol. 72, No. 5, May 2001, pp. 651-658.

* cited by examiner

*Primary Examiner*—Eric S Olson
(74) *Attorney, Agent, or Firm*—Dickstein Shapiro LLP

(57) ABSTRACT

A method for lubricating an implant or graft prior to implantation into a target implant site which enhances the lubricity of the implant or graft and promotes bone growth. The method comprises the steps of lubricating the implant or graft with the composition comprising hyaluronic acid and optionally a growth factor and/or an antiseptic and/or antibiotic, and subsequently implanting the lubricated implant or graft into a target implant site.

6 Claims, 2 Drawing Sheets

METHOD OF APPLYING HYALURONIC ACID TO IMPLANT OR GRAFT TO ENHANCE LUBRICITY AND CELLULAR DENSITY

This application claims the benefit of U.S. Provisional Application Ser. No. 60/402,068, filed Aug. 9, 2002, the entire disclosure of which is incorporated herein by reference.

FIELD OF THE INVENTION

The present invention relates to the field of surgery and, in particular, to a method of applying a composition comprising hyaluronic acid to an implant or a graft to enhance lubricity and cellular density.

BACKGROUND OF THE INVENTION

Patients undergoing surgery requiring temporary or permanent implantation of devices, such as bioabsorbable interference screws or microcell implants, catheters, leads, pacemakers, defibrillators and stents, among many others, are often subjected to implant failure associated with functional problems, for example, the technical capability of the implanted device to adhere to the human tissue and/or bone.

Implants or screws are often used to provide an "interference fit" between tissue and/or bone, in which case tolerances are necessarily tight. In the case of threaded interference screws, for example, substantial torque may be required for insertion. If the screws are formed of non-metal substances, such as PLLA (Poly-(L-Lactic Acid)) or a tricalcium phosphate/hydroxylapatite composite, the socket provided in the screw may strip upon insertion. Accordingly, it would be desirable to lubricate the screw prior to insertion, but only temporarily, so that the screw will not slip within the body after insertion. Additionally, it would be desirable to provide a growth enhancing substance on the screw to accelerate the growth of surrounding bone to the screw, and ultimately, increasing the absorption of the screw by the body. Likewise, it would be desirable to increase the lubricity of a graft during insertion and to promote cell growth between the graft and adjacent bone or tissue.

Hyaluronic acid is a naturally-occurring polysaccharide containing alternating N-acetyl-D-glucosamine and D-glucuronic acid monosaccharide units linked with beta 1-4 bonds and the disaccharide units linked with beta 1-3 glycoside bonds. Hyaluronic acid occurs usually as the sodium salt and has a molecular weight range of about 50,000 to $8 \times 10^6$. Hyaluronic acid is a natural lubricant which breaks down after about 18 hours.

Recently, numerous clinical studies have demonstrated the efficacy and safety of the hyaluronic acid in the treatment of osteoarthritis of the knee and other large joints, particularly for traumatic and degenerative joint diseases. Hyaluronic acid has been shown to increase cellular density, thereby promoting healing of tissue.

SUMMARY OF THE INVENTION

The present invention provides a method for lubricating an implant or graft prior to implantation into a target implant site which enhances the lubricity of the implant or graft (for a limited period of time) and promotes bone growth.

In another aspect, the invention also provides a method of employing a medical implant device in a surgical procedure for which the growth of bone and/or tissue structure is promoted. The method comprises the steps of: (i) lubricating the implant or graft with a lubricating composition comprising hyaluronic acid and optionally a growth factor and/or an antiseptic; and (ii) implanting the lubricated implant or graft into a target implant site. The step of lubricating the implant with the composition can be performed by dispensing the lubricating composition from a syringe.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides a method for lubricating an implant or graft and promoting bone formation by applying a composition comprising hyaluronic acid prior to insertion into a patient's body. The composition comprising hyaluronic acid of the present invention may include additional growth factors and/or antiseptic chemicals to achieve a predetermined lubricity, viscosity and biodegradability.

The term "hyaluronic acid" (HA) as used in the present application refers to hyaluronic acid or salts of hyaluronic acid, such as the sodium, potassium, magnesium and calcium salts, among others. The term "hyaluronic acid" is also intended to include not only elemental hyaluronic acid, but hyaluronic acid with other trace of elements or in various compositions with other elements, as long as the chemical and physical properties of hyaluronic acid remain unchanged. In addition, the term "hyaluronic acid" as used in the present application is intended to include natural formulas, synthetic formulas or combination of these natural and synthetic formulas.

The term "growth factor" as used in the present application is intended to include all factors, such as proteinaceous factors, for example, which play a role in the induction or conduction of growth of bone, ligaments, cartilage or other tissues associated with bone or joints. In particular, these growth factors include bFGF, aFGF, EGF (epidermal growth factor), PDGF (platelet-derived growth factor), IGF (insulin-like growth factor), TGF-$\beta$. I through III, including the TGF-$\beta$, superfamily (BMP-1 through 12, GDF 1 through 12, dpp, 60A, BIP, OF).

Figure 1:
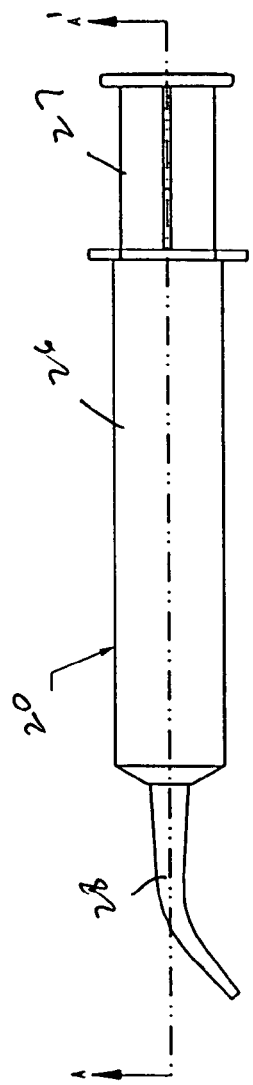
FIG. 1 illustrates a view of a syringe containing a solution comprising hyaluronic acid for lubricating an implant or graft according to an embodiment of the present invention.
Figure 2:
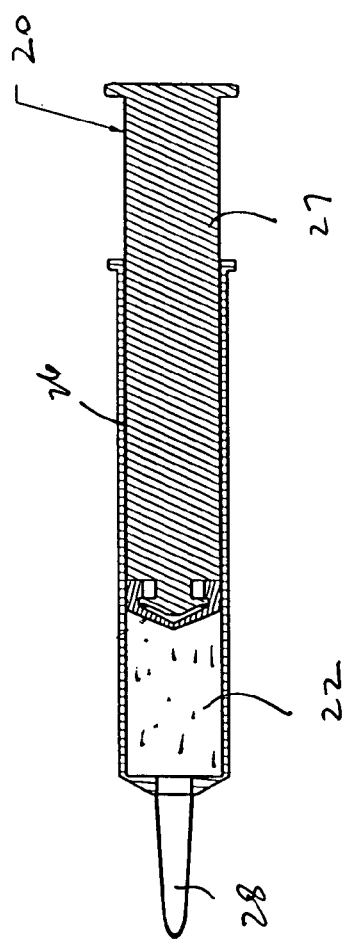
FIG. 2 illustrates a cross-sectional view of the syringe of FIG. 1 taken along line A-A'.

Referring now to the drawings, where like elements are designated by like reference numerals, FIGS. 1 and 2 illustrate an applicator 20 of the present invention, preferably a syringe 20, containing a lubricating bone growth-promoting solution 22 of hyaluronic acid at a predefined concentration by volume. As shown in FIGS. 1 and 2, the syringe 20 comprises a body 26 containing the lubricating bone growth-promoting solution of hyaluronic acid, a plunger 27 and a curved tip 28. The syringe containing hyaluronic acid is preferably packed in a sterile package.

The lubricating bone growth-promoting composition 22 the present invention comprises hyaluronic acid preferably uncrosslinked and having a molecular weight of 500,000 and above, typically in the range of $10^4$ to $10^7$. Optionally, the lubricating bone growth-promoting composition 22 of the present invention may comprise a growth factor and/or an antiseptic chemical and/or an antibiotic. In this case, other solution excipients such as buffer salts, sugars, anti-oxidants and preservatives to maintain the bioactivity of the growth factor and a proper pH of the composition may be also employed. The growth factor and/or the antiseptic and/or the antibiotic will typically be present in the solution in a predetermined concentration range, which will be dependent upon the particular bone site and application, as well as the specific activity of the growth factor and/or the antiseptic and/or the antibiotic.

The lubricating bone growth-promoting composition of the present invention is typically formed as a solution by mixing the hyaluronic acid and the optional growth factor in appropriate amounts so that the hyaluronic acid and the optional growth factor remain in solution at the desired concentration and the solution exhibits the appropriate lubricity, viscosity and biodegradability. For example, the hyaluronic acid may be present in the lubricating bone growth-promoting composition in a range of about 0.1 to about 10% by weight, while the optional growth factor may be present in a range of about 0.1 to about 20% by weight.

Figure 3:
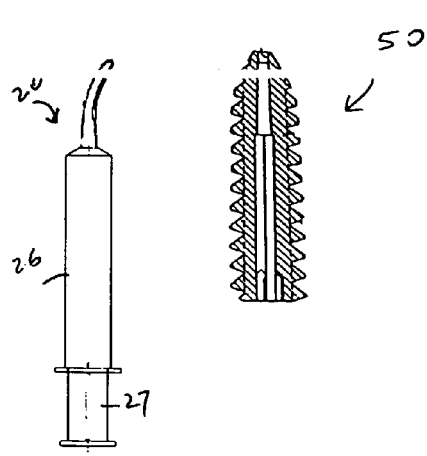
FIG. 3 illustrates the exemplary implant device of FIG. 3 lubricated with the solution contained in the syringe of FIG. 1.
Figure 4:
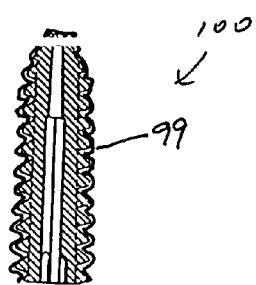
FIG. 4 illustrates the exemplary implant device of FIG. 4 after the lubrication step.

In practice and as illustrated in FIGS. 3 and 4, the syringe 20 of FIG. 1 containing the lubricating bone growth-promoting solution 22 of hyaluronic acid is brought into proximity with a graft or implant, such as a metal interference screw 50, by the surgeon or other assisting person. Plunger 27 of the syringe 20 is depressed such that the lubricating bone growth-promoting solution of hyaluronic acid from the syringe 20 is applied to the metal implant 50 as an exterior coating 99 to form a lubricated implant 100, as illustrated in FIG. 4. Alternatively, the syringe 22 may be used to apply the hyaluronic acid to the graft or into the bone tunnel to which the graft will be secured.

Figure 5:
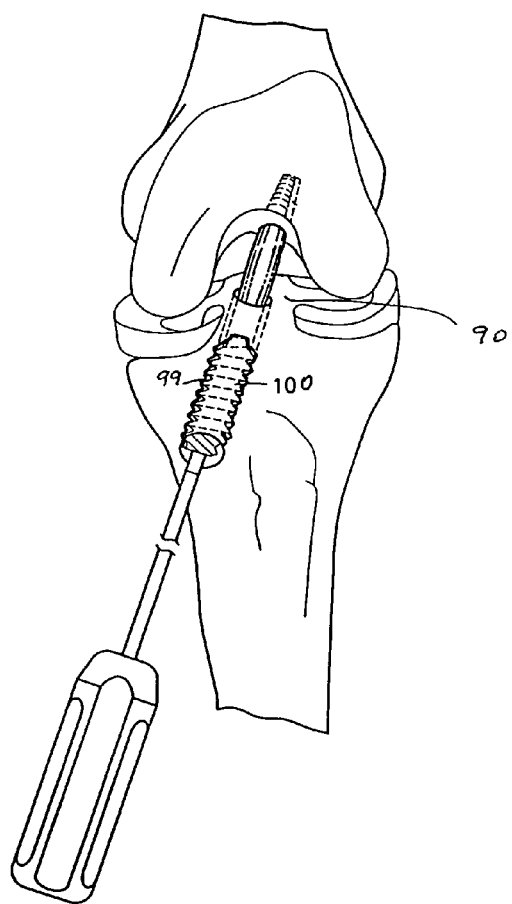
FIG. 5 illustrates the lubricated exemplary implant of FIG. 5 implanted into the tibial tunnel.

FIG. 5 illustrates a cross-sectional view of a tibial tunnel 90 with an interference screw 100 inserted therein. By providing coating 99 of the lubricating bone growth-promoting solution of hyaluronic acid on the interference screw 100, or on the graft, or into the tunnel, the present invention allows a tight interference between the screw and the tunnel while also facilitating insertion (due to the lubricity characteristic of hyaluronic acid, which advantageously dissipates after about 18 hours). Additionally, hyaluronic acid promotes cellular density (re-growth of bone) and thus accelerates healing at the operative site.

Although the above embodiments have been described above with reference to an implantation device, such as the implant 50 of FIG. 3 which is coated with a lubricating bone growth-promoting composition of hyaluronic acid contained in a syringe, such as syringe 20 of FIG. 1, the invention is not limited to this embodiment. Accordingly, the present invention also contemplates an implantation device which is coated with the lubricating bone growth-promoting composition of hyaluronic acid by any means. For example, the implantation device may be coated by inserting the implantation device in an envelope containing the lubricating bone growth-promoting composition of hyaluronic acid, or by submerging the implantation device in a vial filled with the lubricating bone growth-promoting composition of hyaluronic acid, or by using a swab or a wipe impregnated with the lubricating bone growth-promoting composition of hyaluronic acid.

In addition, although the above embodiments have been described above with reference to an interference screw for a particular tissue repair site, such as interference screw 100 inserted into tibial tunnel 90, the invention is not limited to this exemplary embodiment. Accordingly, the present invention has applicability to the fixation of any implant device, such as a graft, a plug, or a screw, for example, which has been coated with a composition comprising hyaluronic acid and which has been inserted in a repair site corresponding to bone, soft tissue or osteochondral tissue, among others.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of lubricating a screw during a tissue repair procedure, the method comprising the steps of:
   providing a syringe containing a composition comprising hyaluronic acid in the proximity of a screw;
   applying hyaluronic acid from the syringe to the screw to allow hyaluronic acid to directly contact the screw to lubricate the screw and to form a lubricated screw prior to insertion of the lubricated screw into a human body; and
   subsequently inserting the lubricated screw into a tissue repair site.

2. The method of claim 1 further comprising the step of positioning the screw in the proximity of the tissue repair site subsequent to the step of applying hyaluronic acid to the screw.

3. The method of claim 1, further comprising the step of implanting the lubricated screw in the tissue repair site.

4. The method of claim 1, wherein the composition comprising hyaluronic acid further comprises a growth factor.

5. The method of claim 4, wherein the composition comprising hyaluronic acid further comprises an antiseptic.

6. The method of claim 1, wherein the screw is an interference screw.

* * * * *